(12) United States Patent
Zheng et al.

(10) Patent No.: US 12,402,847 B2
(45) Date of Patent: Sep. 2, 2025

(54) SCANNING METHOD AND APPARATUS, STORAGE MEDIUM, AND COMPUTER DEVICE

(71) Applicant: Neusoft Medical Systems Co., Ltd., Liaoning (CN)

(72) Inventors: Ling Zheng, Liaoning (CN); Ling Pang, Liaoning (CN)

(73) Assignee: NEUSOFT MEDICAL SYSTEMS CO., LTD., Liaoning (CN)

( * ) Notice: Subject to any disclaimer, the term of this patent is extended or adjusted under 35 U.S.C. 154(b) by 289 days.

(21) Appl. No.: 18/299,028

(22) Filed: Apr. 11, 2023

(65) Prior Publication Data
US 2023/0240629 A1  Aug. 3, 2023

(30) Foreign Application Priority Data
Jul. 26, 2022  (CN) .......................... 202210895426.2

(51) Int. Cl.
*A61B 6/40* (2024.01)
*A61B 6/00* (2006.01)
*A61B 6/58* (2024.01)

(52) U.S. Cl.
CPC .............. *A61B 6/4021* (2013.01); *A61B 6/48* (2013.01); *A61B 6/582* (2013.01)

(58) Field of Classification Search
CPC ......... A61B 6/03; A61B 6/032; A61B 6/0407; A61B 6/4021; A61B 6/48; A61B 6/488; A61B 6/54; A61B 6/582; A61B 6/589
See application file for complete search history.

(56) References Cited

U.S. PATENT DOCUMENTS

| 2015/0010125 | A1 |   | 1/2015 | Sheng et al. |
| 2024/0115226 | A1 | * | 4/2024 | Li ........................ A61B 6/0407 |

FOREIGN PATENT DOCUMENTS

| CN | 112617876 | A |   | 4/2021 |   |
| CN | 113229836 | A |   | 8/2021 |   |
| CN | 113288191 | A |   | 8/2021 |   |
| CN | 113288191 | B | * | 8/2021 | ............. A61B 6/032 |

(Continued)

OTHER PUBLICATIONS

First Office Action dated Jul. 17, 2024 received in corresponding patent family application No. CN202210895426.2. English translation attached.

(Continued)

*Primary Examiner* — David J Makiya
*Assistant Examiner* — Miya Downing (57) ABSTRACT

The present disclosure discloses a scanning method and apparatus, a storage medium, and a computer device. The method includes: obtaining plain film information of a target scanning object, and determining a target bed height based on the plain film information; adjusting the plain film information based on the target bed height to obtain target plain film information; and performing a subsequent operation based on the target plain film information. The present disclosure helps to quickly determine the target bed height, adjust the plain film information based on the target bed height, and perform the subsequent operation based on adjusted plain film information. Thus, a quality of a scanned image is improved while an adjustment efficiency is increased, thereby greatly improving user experience.

20 Claims, 4 Drawing Sheets

(56) References Cited

FOREIGN PATENT DOCUMENTS

CN   114391861 A   4/2022
JP   H05322802 A   12/1993

OTHER PUBLICATIONS

Grant Notice dated Jan. 24, 2025 received in corresponding patent family application No. CN202210895426.2. English translation attached.
Second Office Action dated Oct. 21, 2024 received in corresponding patent family application No. CN202210895426.2. English translation attached.

* cited by examiner

SCANNING METHOD AND APPARATUS, STORAGE MEDIUM, AND COMPUTER DEVICE

CROSS-REFERENCE TO RELATED APPLICATIONS

This application claims a priority to Chinese Patent Application No. CN 202210895426.2 filed on Jul. 26, 2022, the entire disclosure of which is incorporated herein by reference.

FIELD

The present disclosure relates to the field of medical imaging technologies, and more particularly, to a scanning method and apparatus, a storage medium, and a computer device.

BACKGROUND

A Computed Tomography (CT) scanning device is configured to perform spiral scanning imaging or tomographic scanning imaging on a target scanning object to generate a CT image. During scanning performed by the CT scanning device, when a center of a to-be-detected part of the target scanning object is inconsistent with a scanning center of the CT scanning device, the to-be-detected part is likely to be subject to an uneven scanning dose, which directly affects a quality of the CT image.

In order to enable the center of the to-be-detected part of the target scanning object to be consistent with the scanning center of the CT scanning device, a CT scanning operator usually needs to manually operate a positioning lamp of the CT scanning device, and adjusts a bed height based on a marking of the positioning lamp on a side surface of the target scanning object, thus allowing the center of the to-be-detected part of the target scanning object to be approximately consistent with the scanning center of the CT scanning device. However, this method is affected by a human factor, and has low accuracy and efficiency.

SUMMARY

In view of the above problems, the present disclosure provides a scanning method and apparatus, a storage medium, and a computer device, capable of facilitating quickly determining a target bed height, adjusting plain film information based on the target bed height, and performing a subsequent operation based on adjusted plain film information. By doing so, a quality of a scanned image is improved while an adjustment efficiency is increased, thereby greatly improving user experience.

In an aspect of the present disclosure, a scanning method is provided. The scanning method includes: obtaining plain film information of a target scanning object, and determining a target bed height based on the plain film information; adjusting the plain film information based on the target bed height to obtain target plain film information; and performing a subsequent operation based on the target plain film information.

Optionally, the operation of determining the target bed height based on the plain film information includes: determining a position center of a region of interest of the target scanning object in a target direction based on the plain film information, the target direction being a direction perpendicular to a bed surface of a scanning bed; and determining the target bed height based on a positional relation between the position center and a scanning center.

Optionally, the operation of determining the position center of the region of interest of the target scanning object in the target direction based on the plain film information includes: obtaining a target thickness of the region of interest of the target scanning object in the target direction based on the plain film information; and determining the position center of the region of interest of the target scanning object in the target direction based on the target thickness. The plain film information includes a frontal film and/or a lateral film.

Optionally, the operation of obtaining the target thickness of the region of interest of the target scanning object in the target direction based on the plain film information includes: dividing the region of interest indicated by the plain film information into a plurality of sub-regions in a feed direction parallel to the scanning bed, and determining a sub-thickness corresponding to each of the plurality of sub-regions; and obtaining a mean value of the plurality of sub-thicknesses, and determining the mean value of the plurality of sub-thicknesses as the target thickness of the region of interest of the target scanning object in the target direction.

Optionally, the operation of adjusting the plain film information based on the target bed height to obtain the target plain film information includes: determining an adjustment direction of a scanning bed based on the target bed height; determining an adjustment mode of the plain film information based on the adjustment direction; and adjusting the plain film information based on the adjustment mode to obtain the target plain film information.

Optionally, the operation of determining the adjustment mode of the plain film information based on the adjustment direction includes: obtaining a position of a tube focal spot corresponding to the plain film information; determining, based on the adjustment direction when the position of the tube focal spot is on a side of a reference plane, that the adjustment mode of the plain film information is to scale the target scanning object in the plain film information; and determining, based on the adjustment direction when the position of the tube focal spot is on the reference plane, that the adjustment mode of the plain film information is to translate the target scanning object in the plain film information. The reference plane is a plane passing through a scanning center and parallel to a bed surface of the scanning bed.

Optionally, the operation of determining, based on the adjustment direction when the position of the tube focal spot is on the side of the reference plane, that the adjustment mode of the plain film information is to scale the target scanning object in the plain film information includes: determining, when the adjustment direction is a direction in which a distance between the bed surface of the scanning bed and the tube focal spot is increased, that the adjustment mode of the plain film information is to scale down a size of the target scanning object in the plain film information; and determining, when the adjustment direction is a direction in which the distance between the bed surface of the scanning bed and the tube focal spot is reduced, that the adjustment mode of the plain film information is to scale up the size of the target scanning object in the plain film information.

Optionally, the operation of determining, based on the adjustment direction when the position of the tube focal spot is on the reference plane, that the adjustment mode of the plain film information is to translate the target scanning object in the plain film information includes: determining, when the adjustment direction is a direction in which a distance between the bed surface of the scanning bed and a ground is increased, that the adjustment mode of the plain film information is to translate the target scanning object in the plain film information towards a side facing away from the bed surface indicated by the plain film information; and determining, when the adjustment direction is a direction in which the distance between the bed surface of the scanning bed and the ground is reduced, that the adjustment mode of the plain film information is to translate the target scanning object in the plain film information towards a side adjacent to the bed surface indicated by the plain film information.

Optionally, a scaling ratio of the operation of scaling the target scanning object in the plain film information and a translation distance of the operation of translating the target scanning object in the plain film information are both positively correlated with a difference between the target bed height and an actual bed height of the scanning bed when obtaining the plain film information.

Optionally, the operation of adjusting the plain film information based on the target bed height to obtain the target plain film information includes updating a bed height and/or a bed calibration in the plain film information based on the target bed height to obtain the target plain film information.

Optionally, the operation of performing the subsequent operation based on the target plain film information includes: selecting a positioning box based on the target plain film information; obtaining scanning parameter information based on the positioning box, the scanning parameter information including a start scanning position and an end scanning position; and adjusting an actual bed height of a scanning bed based on the target bed height, and then performing an axial scanning or a spiral scanning based on the scanning parameter information.

In another aspect of the present disclosure, a scanning apparatus is provided. The scanning apparatus includes: a target bed height obtaining module configured to obtain plain film information of a target scanning object, and determine a target bed height based on the plain film information; a plain film information adjustment module configured to adjust the plain film information based on the target bed height to obtain target plain film information; and an execution module configured to perform a subsequent operation based on the target plain film information.

Optionally, the target bed height obtaining module includes: a position center determining unit configured to determine a position center of a region of interest of the target scanning object in a target direction based on the plain film information, the target direction being a direction perpendicular to a bed surface of a scanning bed; and a target bed height determining unit configured to determine the target bed height based on a positional relation between the position center and a scanning center.

Optionally, the position center determining unit is configured to: obtain a target thickness of the region of interest of the target scanning object in the target direction based on the plain film information; and determine the position center of the region of interest of the target scanning object in the target direction based on the target thickness. The plain film information includes a frontal film and/or a lateral film.

Optionally, the position center determining unit is further configured to: divide the region of interest indicated by the plain film information into a plurality of sub-regions in a feed direction parallel to the scanning bed, and determine a sub-thickness corresponding to each of the plurality of sub-regions; and obtain a mean value of the plurality of sub-thicknesses, and determine the mean value of the plurality of sub-thicknesses as the target thickness of the region of interest of the target scanning object in the target direction.

Optionally, the plain film information adjustment module includes: a first determining unit configured to determine an adjustment direction of a scanning bed based on the target bed height; a second determining unit configured to determine an adjustment mode of the plain film information based on the adjustment direction; and a third determining unit configured to adjust the plain film information based on the adjustment mode to obtain the target plain film information.

Optionally, the second determining unit is configured to: obtain a position of a tube focal spot corresponding to the plain film information; determine, based on the adjustment direction when the position of the tube focal spot is on a side of a reference plane, that the adjustment mode of the plain film information is to scale the target scanning object in the plain film information; and determine, based on the adjustment direction when the position of the tube focal spot is on the reference plane, that the adjustment mode of the plain film information is to translate the target scanning object in the plain film information. The reference plane is a plane passing through a scanning center and parallel to a bed surface of the scanning bed.

Optionally, the second determining unit is further configured to: determine, when the adjustment direction is a direction in which a distance between the bed surface of the scanning bed and the tube focal spot is increased, that the adjustment mode of the plain film information is to scale down a size of the target scanning object in the plain film information; and determine, when the adjustment direction is a direction in which the distance between the bed surface of the scanning bed and the tube focal spot is reduced, that the adjustment mode of the plain film information is to scale up the size of the target scanning object in the plain film information.

Optionally, the second determining unit is further configured to: determine, when the adjustment direction is a direction in which a distance between the bed surface of the scanning bed and a ground is increased, that the adjustment mode of the plain film information is to translate the target scanning object in the plain film information towards a side facing away from the bed surface indicated by the plain film information; and determine, when the adjustment direction is a direction in which the distance between the bed surface of the scanning bed and the ground is reduced, that the adjustment mode of the plain film information is to translate the target scanning object in the plain film information towards a side adjacent to the bed surface indicated by the plain film information.

Optionally, a scaling ratio of the operation of scaling the target scanning object in the plain film information and a translation distance of the operation of translating the target scanning object in the plain film information are both positively correlated with a difference between the target bed height and an actual bed height of the scanning bed when obtaining the plain film information.

Optionally, the plain film information adjustment module is further configured to update a bed height and/or a bed calibration in the plain film information based on the target bed height to obtain the target plain film information.

Optionally, the execution module is configured to: select a positioning box based on the target plain film information; obtain scanning parameter information based on the positioning box, the scanning parameter information including a start scanning position and an end scanning position; and adjust an actual bed height of a scanning bed based on the target bed height, and then perform an axial scanning or a spiral scanning based on the scanning parameter information.

In yet another aspect of the present disclosure, a storage medium is provided. The storage medium stores a computer program. The computer program, when executed by a processor, implements the scanning method described above.

In still yet another aspect of the present disclosure, a computer device is provided. The computer device includes a storage medium, a processor, and a computer program stored in the storage medium and executable by the processor. The processor, when executing the computer program, implements the scanning method described above.

Through the technical solutions described above, according to the scanning method and apparatus, the storage medium, and the computer device provided by the present disclosure, the target bed height of the scanning bed is determined based on the plain film information, and then the plain film information is adjusted based on the determined target bed height to obtain the target plain film information. Later, a user can perform the subsequent operation based on the target plain film information. According to the embodiments of the present disclosure, a quality of a scanned image is improved while an adjustment efficiency is increased, thereby greatly improving user experience.

The above description is merely an overview of the technical solutions of the present disclosure. To facilitate a clear understanding of technical approaches of the present disclosure, the technical solutions can be performed in accordance with the contents of the specification. Meanwhile, to clarify and explain the above and other objects, features, and advantages of the present disclosure, specific implementations of the present disclosure will be described below.

BRIEF DESCRIPTION OF THE DRAWINGS

The accompanying drawings described herein are used to provide a further understanding of the present disclosure and constitute a part of the present disclosure. Exemplary embodiments of the present disclosure and description thereof are used to explain the present disclosure, and do not constitute an improper limitation of the present disclosure.

DETAILED DESCRIPTION

The present disclosure will be described in detail below with reference to the accompanying drawings and in conjunction with embodiments. It should be noted that, the embodiments of the present disclosure and features in the embodiments can be combined with each other without any conflict.

Figure 1:
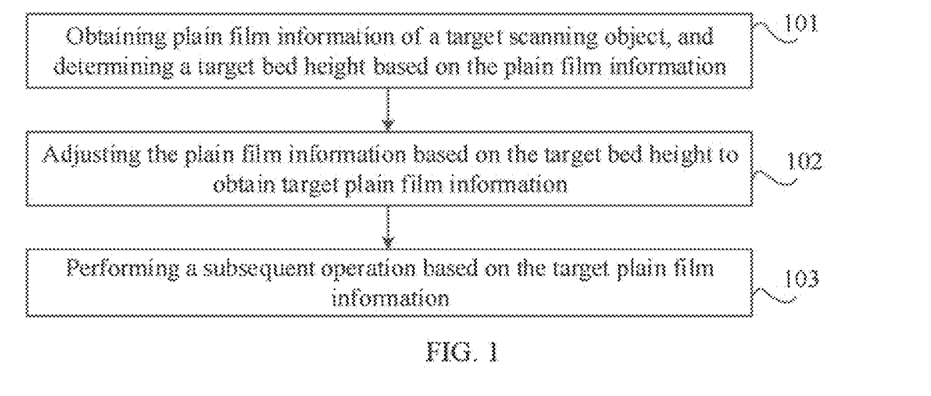
FIG. 1 illustrates a flowchart of a scanning method according to an embodiment of the present disclosure.

Embodiments of the present disclosure provide a scanning method. The method includes operations at block 101 to block 103 as illustrated in FIG. 1.

At block 101, plain film information of a target scanning object is obtained, and a target bed height is determined based on the plain film information.

The plain film information is generally used to determine a position of a region of interest of the target scanning object, and provide a basis for setting of scanning parameters of subsequent scanning. The plain film information can be obtained by a CT scanning equipment, a Magnetic Resonance Imaging (MRI) equipment, a Positron Emission Tomography (PET) equipment, etc. Taking CT scanning as an example, the plain film information of the target scanning object is obtained by a CT scanning device. The target scanning object may be a person, an animal, etc., or may also be a part of a person or an animal. The plain film information may include a plain film image or plain film Digital Imaging and Communications in Medicine (DICOM) header file information, etc. The plain film image may be at least one of a frontal film or a lateral film. The frontal film and the lateral film are collectively referred to as double plain films. The target bed height may be determined based on the plain film information. A manner to determine the target bed height will be described in detail below.

At block 102, the plain film information is adjusted based on the target bed height to obtain target plain film information.

Further, the target bed height is determined, and then a bed height of the scanning bed may be adjusted to the target bed height. After the bed height of the scanning bed is adjusted to the target bed height, a scanning center height of the CT scanning device is consistent with that of a center of the target scanning object. A positional relation between a tube focal spot and the target scanning object will change with a variation of the bed height. Therefore, the plain film information obtained at different bed heights is different. Hence, after an actual bed height of the scanning bed is adjusted, the plain film information needs to be adjusted. Later, a doctor can perform a positioning box selection or other operations on the adjusted plain film information to ensure accuracy of scanning information. The adjusted plain film information is the target plain film information. An adjustment of the plain film information includes an adjustment of at least one of a size of the target scanning object, a position of the target scanning object, an update of a bed calibration, or an update of a bed height in the plain film information.

At block 103, a subsequent operation is performed based on the target plain film information.

The subsequent operation includes, but is not limited to, a positioning box selection and a CT spiral scanning or a CT axial scanning based on the positioning box.

By applying the technical solutions of the embodiments, the target bed height of the scanning bed is determined based on the plain film information, and the plain film information is adjusted based on the determined target bed height to obtain the target plain film information. Later, a user can perform the subsequent operation by using the target plain film information. According to the embodiments of the present disclosure, a quality of a scanned image is improved while an adjustment efficiency is increased, thereby greatly improving user experience.

Figure 2:
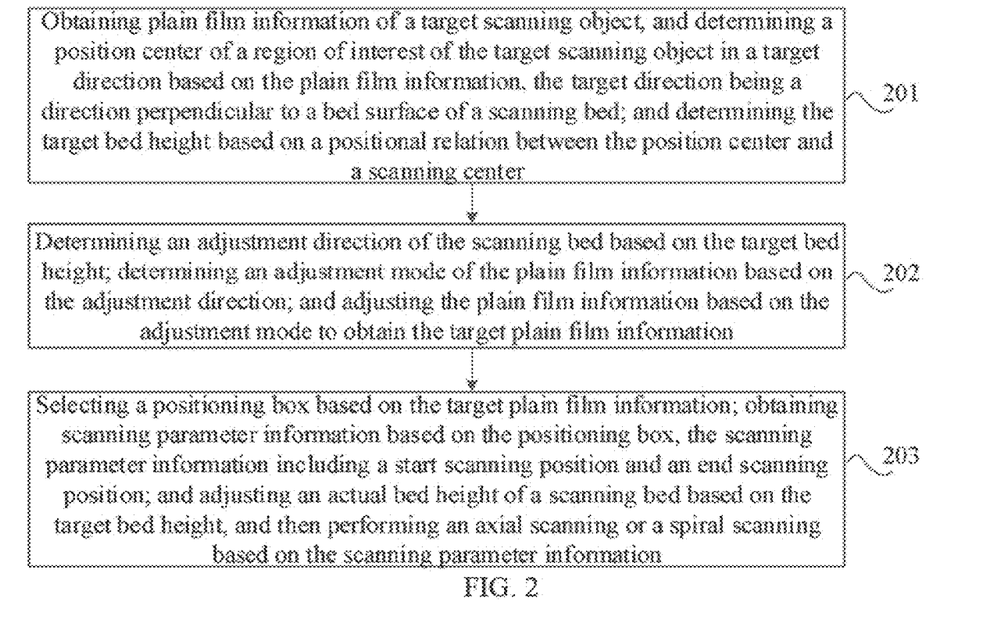
FIG. 2 illustrates a flowchart of another scanning method according to an embodiment of the present disclosure.

Further, as a refinement and extension of detailed implementations of the above embodiments, another scanning method is provided to completely illustrate a specific implementation process of the embodiments. The method includes operations at block 201 to block 203 as illustrated in FIG. 2.

At block 201, plain film information of a target scanning object is obtained, and a position center of a region of interest of the target scanning object in a target direction is determined based on the plain film information, the target direction being a direction perpendicular to a bed surface of a scanning bed; and the target bed height is determined based on a positional relation between the position center and a scanning center.

In the above embodiments, the target direction may be preset, which may be the direction perpendicular to the bed surface of the scanning bed. As an example, in a CT scanning, the target scanning object is scanned by the CT scanning device to obtain corresponding plain film information. After the plain film information is determined, the position center of the region of interest of the target scanning object in the target direction may be determined based on the plain film information. For example, when the target scanning object lies flat on the scanning bed, the position center refers to a center of a thickness of the target scanning object; and when the target scanning object lies on sideways on the scanning bed, the position center refers to a center of a width of the target scanning object. As an example, when the target scanning object is a person, the thickness of the target scanning object refers to a distance in a direction from the chest to the back of the person, and the width of the target scanning object refers to a distance in a direction from the left hand to the right hand of the person. After the position center of the region of interest of the target scanning object in the target direction is determined, the target bed height of the scanning bed may be determined based on the position center and the scanning center.

At block 202, an adjustment direction of the scanning bed is determined based on the target bed height: an adjustment mode of the plain film information is determined based on the adjustment direction; and the plain film information is adjusted based on the adjustment mode to obtain the target plain film information.

In this embodiment, the target bed height is determined, and then the adjustment direction of the scanning bed may be determined based on the target bed height. The adjustment direction of the scanning bed may include an upward adjustment direction, i.e., adjusting higher, and also a downward adjustment direction, i.e., adjusting lower. Then the adjustment mode of the plain film information may be further determined based on the adjustment direction of the scanning bed. The plain film information is adjusted based on the adjustment mode to obtain the adjusted plain film information, i.e., the target plain film information.

When the target bed height is determined, the bed height of the scanning bed needs to be adjusted subsequently to the target bed height. When the bed height of the scanning bed is adjusted to the target bed height, the scanning center height of the CT scanning device is consistent with that of the position center of the region of interest of the target scanning object. However, the plain film information corresponding to the target scanning object is still the initial plain film information. Therefore, when the doctor selects a position of the positioning box on the plain film later to scan the target scanning object again, it is inappropriate to directly scan the target scanning object under such a condition that each piece of position information in the plain film is the initial position information. In this way, the plain film information may be adjusted to obtain the target plain film information, and the CT scanning is performed on the target scanning object based on the target plain film information, which eliminates a need to rescan the target scanning object to obtain the target plain film after the bed height is adjusted to the target bed height, reducing a scanning dose for the target scanning object.

At block 203, a positioning box is selected based on the target plain film information; scanning parameter information is obtained based on the positioning box, the scanning parameter information including a start scanning position and an end scanning position; and an actual bed height of a scanning bed is adjusted based on the target bed height, and then an axial scanning or a spiral scanning is performed based on the scanning parameter information.

In this embodiment, the plain film information is adjusted to obtain the target plain film information, and then the user may select the positioning box based on the target plain film information. In this embodiment, after the user selects the positioning box, the scanning parameter information may be determined based on the selected positioning box. The scanning parameter information may include the start scanning position and the end scanning position, and may also include other scanning parameter information. After the scanning parameter information is determined, when the scanning bed has been adjusted to the target bed height, the CT spiral scanning or the CT axial scanning may be performed on the target scanning object based on the scanning parameter information.

Optionally, the operation of "determining a position center of a region of interest of the target scanning object in a target direction based on the plain film information" described at block 201 includes: obtaining a target thickness of the region of interest of the target scanning object in the target direction based on the plain film information; and determining the position center of the region of interest of the target scanning object in the target direction based on the target thickness. The plain film information includes a frontal film and/or a lateral film.

In this embodiment, the plain film information is obtained, and then the target thickness of the region of interest of the target scanning object in the target direction may be further identified from the plain film information. A position indicated by a half of the target thickness is determined as the position center of the target scanning object.

Optionally, the operation of "determining the target bed height based on a positional relation between the position center and a scanning center" described at block 201 includes: determining the target bed height based on a height difference between a height of the scanning center and a height of the position center.

Figure 3:
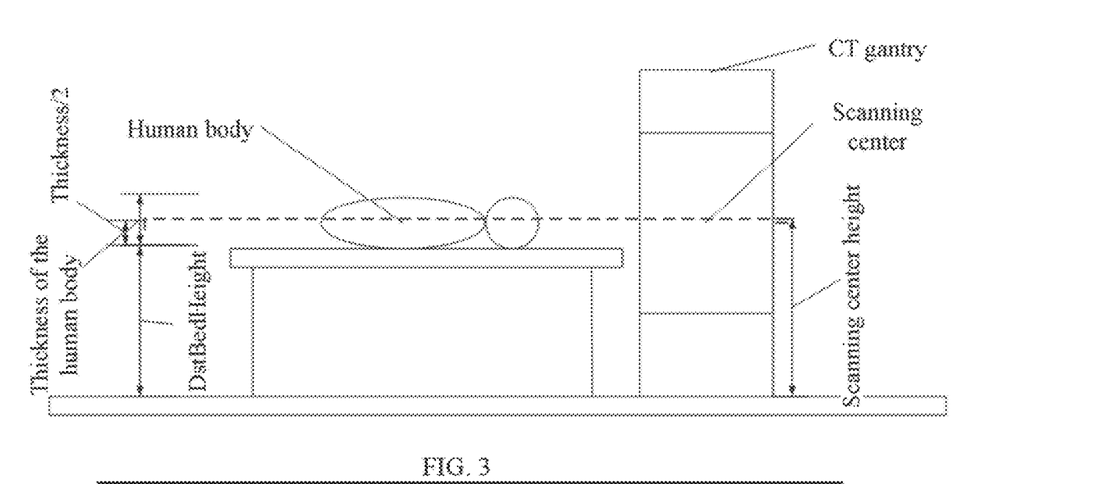
FIG. 3 illustrates a schematic diagram of a scanning case according to an embodiment of the present disclosure.

In this embodiment, FIG. 3 reveals that a sum of the target bed height and the height of the position center of the region of interest of the target scanning object is equal to the scanning center height of the CT scanning device. The position center refers to the position indicated by the half of the target thickness. Therefore, the half of the target thickness may be determined as a half thickness. A difference obtained by subtracting the half thickness from the scanning center height of the CT scanning device is a to-be-adjusted height of the scanning bed. When the scanning center height of the CT scanning device is inconsistent with the position center of the region of interest of the target scanning object, an uneven scanning dose is likely to occur during the CT scanning performed on the target scanning object, which affects the quality of the CT image. Therefore, the target bed height of the scanning bed may be determined based on the target thickness of the region of interest of the target scanning object and the scanning center height of the CT scanning device. In this way, when the target scanning object is at the target bed height, the position center of the region of interest of the target scanning object can be consistent with the scanning center height of the CT scanning device, thus greatly improving the quality of the CT image. The scanning center height of the CT scanning device is fixed and known. As illustrated in FIG. 3, the target scanning object is a human body, and the target thickness is a human body thickness, then target bed height=scanning center height-(half of the human body thickness). Therefore, when the human body thickness is determined, the target bed height can be determined accordingly.

In the embodiments of the present disclosure, optionally, the operation of "obtaining the target thickness of the region of interest of the target scanning object in the target direction based on the plain film information" includes: inputting the plain film information into a trained deep learning model; and obtaining the target thickness of the region of interest of the target scanning object in the target direction based on an output of the deep learning model.

In this embodiment, for the CT scanning device, a scanning ray is emitted from a tube. That is, the position of the tube focal spot determines a position from which the ray is emitted. Here, a reference plane is preset. The reference plane refers to a plane passing through the scanning center and parallel to the bed surface of the scanning bed. In a case where the position of the tube focal spot is on a side of the reference plane when the plain film information is obtained, for example, when the tube is at a scanning angle of 0° or 180°, a region of interest displayed in the plain film is a projection of the target scanning object on a plane parallel to the bed surface of the scanning bed, and relevant information about the target thickness cannot be seen from the region of interest of the plain film, regardless of whether the target scanning object is in a state of lying flat or a state of lying on sideways. In this case, the plain film information can be input into the trained deep learning model. In some embodiments, the plain film may be divided into different sub-regions. It is assumed that a direction perpendicular to the ground corresponds to a coordinate axis of y-axis, a direction in which the scanning bed moves backwards and forwards represents a z-axis, the other direction represents an x-axis, and a plane formed by the z-axis and the x-axis is parallel to the ground. In this case, the plain film may be divided based on a direction parallel to the x-axis or a direction parallel to the z-axis. Then divided sub-regions may be input into the trained deep learning model to obtain a sub-thickness in the y-axis direction corresponding to each sub-region. Finally, a mean value of sub-thicknesses corresponding to different sub-regions can be obtained and determined as the target thickness of the target scanning object. The deep learning model may be obtained by training a sample input set and a sample output set. The sample input set may be sample sub-regions obtained by dividing a sample plain film. The sample output set may be real thicknesses corresponding to respective sample sub-regions. In this case, each sample plain film in the sample input set is obtained when the position of the tube focal spot is on a side of the reference plane. Based on the deep learning model, target thickness information unavailable on the plain film can be determined simply and conveniently in a case where the region of interest in the plain film is the projection of the target scanning object on the plane parallel to the bed surface.

Since scanning demands are different, demands for plain film information are also different. For example, when the target scanning object is in the state of lying flat, the target thickness may be directly determined based on the lateral film of the target scanning object, but it is actually necessary to further determine the region of interest of the target scanning object based on the frontal film. Thus, to avoid scanning the target scanning object twice, the position of the tube focal spot may be positioned on the side of the reference plane to obtain the plain film information. In this case, the target thickness of the region of interest of the target scanning object can be determined in the above manner.

In addition, when the position of the tube focal spot is on the reference plane, i.e., when the tube is at a scanning angle of 90° or 270°, the plain film information can also be input into the trained deep learning model. After the plain film information is inputted into the trained deep learning model, the target thickness of the region of interest of the target scanning object in the target direction may be determined based on an output of the deep learning model. A method used in this case is the same as that described above.

In the embodiments of the present disclosure, optionally, the operation of "obtaining the target thickness of the region of interest of the target scanning object in the target direction based on the plain film information" further includes: dividing the region of interest indicated by the plain film information into a plurality of sub-regions in a feed direction parallel to the scanning bed, and determining a sub-thickness corresponding to each of the plurality of sub-regions; and obtaining a mean value of the plurality of sub-thicknesses, and determining the mean value of the plurality of sub-thicknesses as the target thickness of the region of interest of the target scanning object in the target direction.

Figure 4:
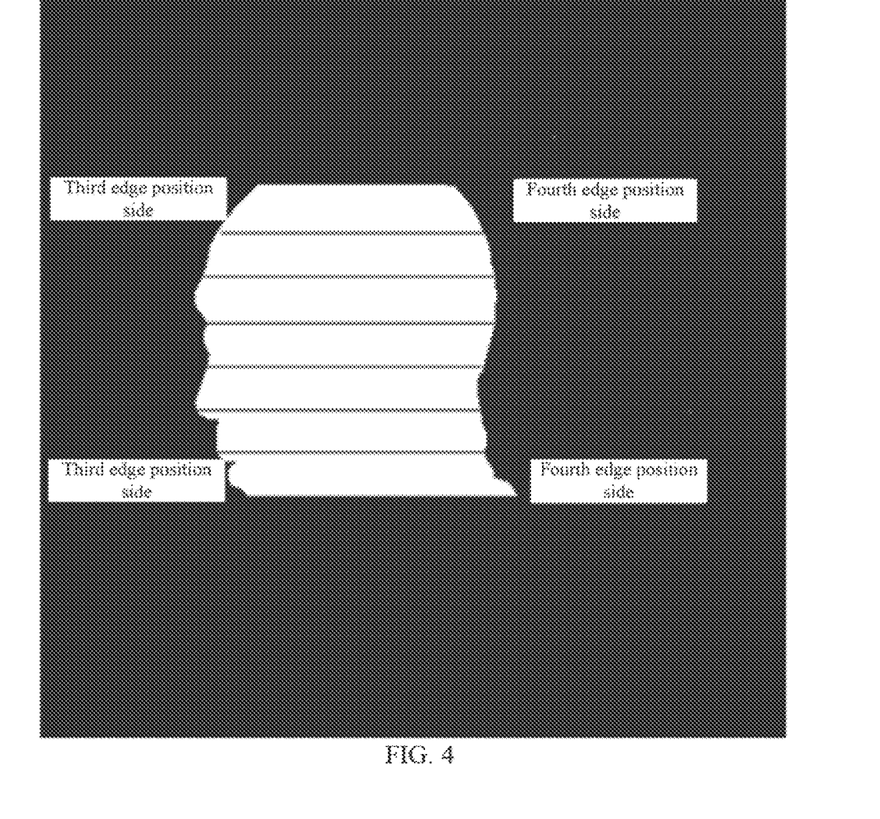
FIG. 4 illustrates a schematic diagram of a plain film division according to an embodiment of the present disclosure.

In this embodiment, when the position of the tube focal spot is on the reference plane during the plain film information is obtained, the target thickness can also be determined by using the following method. In this case, similarly, the region of interest indicated by the plain film information may be divided, specifically in a direction parallel to the target direction. A plurality of sub-regions may be obtained after the division. As illustrated in FIG. 4, the position of the tube focal spot is on the reference plane when the plain film information is obtained, the target scanning object on the scanning bed is in the state of lying flat, and a lateral film of a target scanned image is obtained through a scanning. The region of interest in the plain film may be divided based on the feed direction parallel to the scanning bed. A spacing for the division may be predetermined and equal. Then, a third edge position and a fourth edge position may be identified from each sub-region. The third edge position and the fourth edge position are edge positions parallel to the target direction, and may specifically be positions of pixels on edges. Since each sub-region is spaced apart from one another, positions of all the pixels on a third edge can be summed and averaged to obtain the third edge position, and similarly, the fourth edge position can be obtained. In FIG. 4, the third edge position is identified from a left side of each sub-region, and the fourth edge position is identified from a right side of each sub-region. After the third edge position and the fourth edge position that correspond to each sub-region are determined, a difference between the third edge position and the fourth edge position can be calculated. When the difference corresponding to a sub-region is a positive value, the difference is the sub-thickness of this sub-region. When the difference is a negative value, an absolute value of the difference is the sub-thickness of this sub-region. In some embodiments, the difference between the third edge position and the fourth edge position may be a number difference of pixels. The sub-thickness of this sub-region can be obtained by multiplying the number difference by a real physical size corresponding to each pixel. In addition, the third edge position may also be determined as a side having a larger coordinate value on a coordinate axis, and the fourth edge position may be determined as a side having a smaller coordinate value on the coordinate axis. Thus, the sub-thickness of the corresponding sub-region may be directly determined based on the difference between the third edge position and the fourth edge position. Finally, a mean value of the sub-thicknesses of all the sub-regions may be determined based on the sub-thickness corresponding to each sub-region. The mean value is determined as the target thickness of the region of interest of the target scanning object in the target direction.

In the embodiments of the present disclosure, optionally, the operation of "determining an adjustment mode of the plain film information based on the adjustment direction" described at block 202 includes: obtaining a position of a tube focal spot corresponding to the plain film information; determining, based on the adjustment direction when the position of the tube focal spot is on a side of a reference plane, that the adjustment mode of the plain film information is to scale the target scanning object in the plain film information; and determining, based on the adjustment direction when the position of the tube focal spot is on the reference plane, that the adjustment mode of the plain film information is to translate the target scanning object in the plain film information. The reference plane is the plane passing through the scanning center and parallel to the bed surface of the scanning bed. In the embodiments of the present disclosure, optionally, a scaling ratio of the operation of scaling the target scanning object in the plain film information and a translation distance of the operation of translating the target scanning object in the plain film information are both positively correlated with a difference between the target bed height and an actual bed height of the scanning bed when obtaining the plain film information.

In this embodiment, before the adjustment mode of the plain film information is determined, the position of the tube focal spot may be determined when the plain film information is obtained, i.e., a position from which a ray is emitted may be determined when the plain film information is obtained. When the position of the tube focal spot is on the side of the reference plane, the adjustment mode of the plain film information may be determined, based on the adjustment direction, as scaling the target scanning object in the plain film information. When the position of the tube focal spot is on the reference plane, the adjustment mode of the plain film information may be determined, based on the adjustment direction, as translating the target scanning object in the plain film information. For example, the target scanning object is in the state of lying flat on the scanning bed. In a case where the position of the tube focal spot is on the side of the reference plane when the plain film information is obtained, the region of interest displayed by the plain film is the projection of the target scanning object on the plane parallel to the bed surface of the scanning bed. When the bed height is adjusted, a distance between the tube focal spot and the target scanning object may change in a ray emission direction of the tube. Therefore, when the plain film information is adjusted, the region of interest of the target scanning object may be scaled. In a case where the position of the tube focal spot is on the reference plane when the plain film information is obtained, the distance between the tube focal spot and the target scanning object may not change in the ray emission direction of the tube after the bed height is adjusted, but the target scanning object is translated relative to the tube focal spot in a height direction of the scanning bed. Therefore, when the plain film information is adjusted, the region of interest of the target scanning object may be translated. In this embodiment, a beam emitted by the tube is a fan-shaped beam or a conical beam, and the ray emission direction of the tube may be a direction indicated by a center of the fan-shaped beam or a center of the conical beam. The scaling ratio of the operation of scaling the target scanning object in the plain film information and the translation distance of the operation of translating the target scanning object in the plain film information are both positively correlated with the difference between the target bed height and the actual bed height of the scanning bed when obtaining the plain film information.

In the embodiments of the present disclosure, optionally, the operation of "determining, based on the adjustment direction when the position of the tube focal spot is on a side of a reference plane, that the adjustment mode of the plain film information is to scale the target scanning object in the plain fil information" includes: determining, when the adjustment direction is a direction in which a distance between the bed surface of the scanning bed and the tube focal spot is increased, that the adjustment mode of the plain film information is to scale down a size of the target scanning object in the plain film information; and determining, when the adjustment direction is a direction in which the distance between the bed surface of the scanning bed and the tube focal spot is reduced, that the adjustment mode of the plain film information is to scale up the size of the target scanning object in the plain film information.

In this embodiment, when the position of the tube focal spot is on the side of the reference plane and located on a lower side of the reference plane, i.e., below the bed surface of the scanning bed, in a case where the adjustment direction of the scanning bed is a direction in which a distance between the bed surface of the scanning bed and the ground is increased, i.e., the height of the scanning bed is raised and the distance between tube focal spot and the bed surface of the scanning bed is increased, scaling down the size of the target scanning object in the plain film information may be determined as the adjustment mode of the plain film information. On the contrary, in a case where the adjustment direction of the scanning bed is a direction in which the distance between the bed surface of the scanning bed and the ground is reduced, i.e., the height of the scanning bed is lowered and the distance between the tube focal spot and the bed surface of the scanning bed is reduced, scaling up the size of the target scanning object in the plain film information may be determined as the adjustment mode of the plain film information.

In some embodiments, sizes for scaling down and scaling up may be determined based on: calculating a first distance and a second distance, the first distance being a distance between the tube focal spot and the position center of the region of interest of the target scanning object when obtaining the plain film information, and the second distance being a distance between the tube focal spot and the scanning center, i.e., a distance between the position center of the region of interest of the target scanning object and the tube focal spot after the scanning bed is adjusted to the target bed height; and determining a first adjustment size based on the first distance and the second distance.

Figure 5:
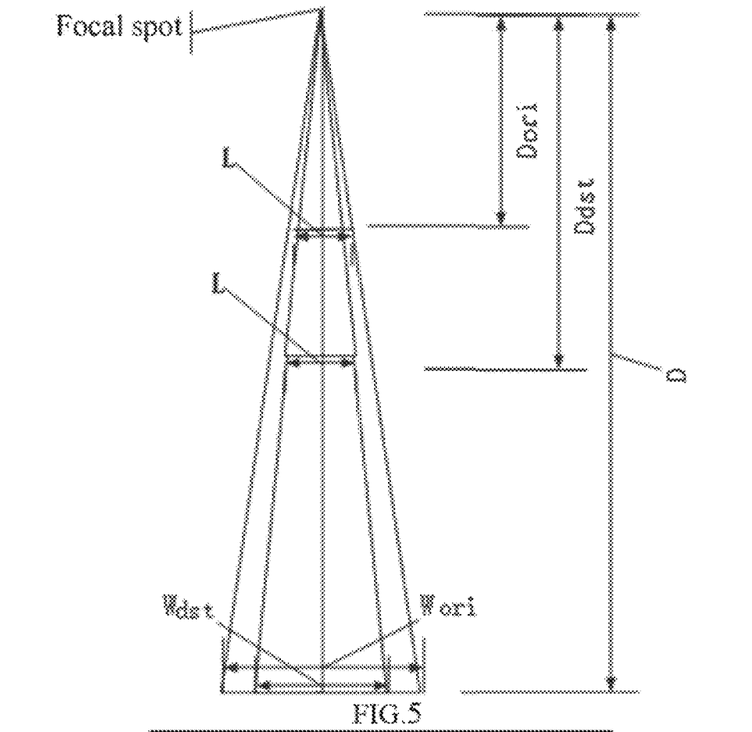
FIG. 5 illustrates a schematic diagram of an imaging relation according to an embodiment of the present disclosure.

In this embodiment, the first distance and the second distance may be calculated separately when determining the sizes for scaling down and scaling up (i.e., the first adjustment size). The first distance may be a difference between a height of the tube focal spot and a height of the position center of the region of interest of the target scanning object when the plain film information is obtained. In some embodiments, assuming that a height of the scanning bed is an initial bed height when the plain film information is obtained, the height of the position center of the region of interest of the target scanning object when the plain film information is obtained may refer to a height of the position center of the region of interest of the target scanning object from the ground, i.e., initial bed height+target thickness/2, thus the first distance=height of the tube focal spot−initial bed height−target thickness/2. Meanwhile, the second distance may be a difference between the height of the tube focal spot and the height of the scanning center. In some embodiments, the height of the scanning center may be an actual physical height of the scanning center when a system is set. Since the scanning center coincides with the position center of the region of interest of the target scanning object at the target bed height, the scanning center may also be equal to target bed height+target thickness/2, thus the second distance=height of the tube focal spot−target bed height−target thickness/2. After the first distance and the second distance are determined, a product between the first distance and a scanning width and a ratio of the product to the second distance may be calculated, and finally the first adjustment size is determined based on the ratio. In particular, the first adjustment size may be determined based of the following formula:

$$W_{dst} = \frac{D_{ori} * V_{ori}}{D_{dst}},$$

where $W_{dst}$ represents the first adjustment size, $W_{ori}$ represents the scanning width, $D_{dst}$ represents the second distance, and $D_{ori}$ represents the first distance. In some embodiments, as illustrated in FIG. 5, in a case where the position of the tube focal spot is on the side of the reference plane when the plain film information is obtained, and a patient is in the state of lying flat, the position of the tube focal spot remains unchanged. When the bed height of the scanning bed is the initial bed height, $D_{ori}$ represents a distance between a height of the position of the tube focal spot and a height of a position center of a region of interest of the patient at the initial bed height, i.e., the first distance, L represents an actual human body width at a scanning position, D represents a distance between the tube focal spot and a detector, and Wo represents a scanning width of the target scanning object in the plain film information obtained at the initial bed height, thus $$\frac{D_{ori}}{L/2} = \frac{D}{W_{ori}/2}.$$

When the bed height of the scanning bed is the target bed height, $D_{dst}$ represents a distance between the height of the tube focal spot and the height of the position center of the region of interest of the patient at the target bed height, i.e., the second distance, L represents the actual human body width at the scanning position, D represents the distance between the tube focal spot and the detector, and Was represents the scanning width of the target scanning object in the plain film information obtained at the target bed height, i.e., the first adjustment size, thus $$\frac{D_{dst}}{L/2} = \frac{D}{W_{dst}/2}.$$

Since the state of the target scanning object in the scanning bed remains unchanged, the actual human body width corresponding to the target scanning object also remains unchanged. After a transformation, $D_{dst}*W_{ori}=D_{dst}*(L/2)$ and $D_{ori}*W_{ori}=D*(L/2)$ can be obtained. Thus, $D_{ori}*W_{ori}=D*W_{dst}$. Therefore, when the plain film information is adjusted to plain film information corresponding to the target bed height, the first adjustment size may be $$W_{dst} = \frac{D_{ori} * V_{ori}}{D_{dst}},$$

In the embodiments of the present disclosure, optionally, a method for obtaining the scanning width of the target scanning object includes: identifying a first edge position and a second edge position of the region of interest indicated by the plain film information, and determining the scanning width of the target scanning object in the plain film information based on a difference between the first edge position and the second edge position.

In addition, the region of interest indicated in the plain film information may be further identified to determine the first edge position and the second edge position of the region of interest in an x-axis direction. It may be set that the direction perpendicular to the ground corresponds to the coordinate axis of y-axis, the direction in which the scanning bed moves backwards and forwards represents the z-axis, and the other direction represents the x-axis. For example, when the target scanning object lies flat on the scanning bed, and a scanning position is the head of the target scanning object, the plain film is the anteroposterior film, in which case the first edge position and the second edge position in the plain film in the x-axis direction may be positions of the left ear and the right ear of the patient in the plain film; and when the target scanning object lies on sideways on the scanning bed, and the scanning position is the head of the target scanning object, the plain film is the lateral film, in which case the first edge position and the second edge position in the plain film in the x-axis direction may be positions of the nose and the back of the head of the patient in the plain film. The first edge position and the second edge position of the region of interest are identified, and then the difference between the first edge position and the second edge position may be calculated. The difference between the first edge position and the second edge position may also be a number difference of pixels. A product calculated based on the number difference of pixels and a real physical size corresponding to each pixel is determined as the scanning width of the target scanning object in the plain film.

In the embodiments of the present disclosure, optionally, the operation of "determining, based on the adjustment direction when the position of the tube focal spot is on the reference plane, that the adjustment mode of the plain film information is to translate the target scanning object in the plain film information" includes: determining, when the adjustment direction is a direction in which a distance between the bed surface of the scanning bed and a ground is increased, that the adjustment mode of the plain film information is to translate the target scanning object in the plain film information towards a side facing away from the bed surface indicated by the plain film information; and determining, when the adjustment direction is a direction in which the distance between the bed surface of the scanning bed and the ground is reduced, that the adjustment mode of the plain film information is to translate the target scanning object in the plain film information towards a side adjacent to the bed surface indicated by the plain film information.

Figure 6:
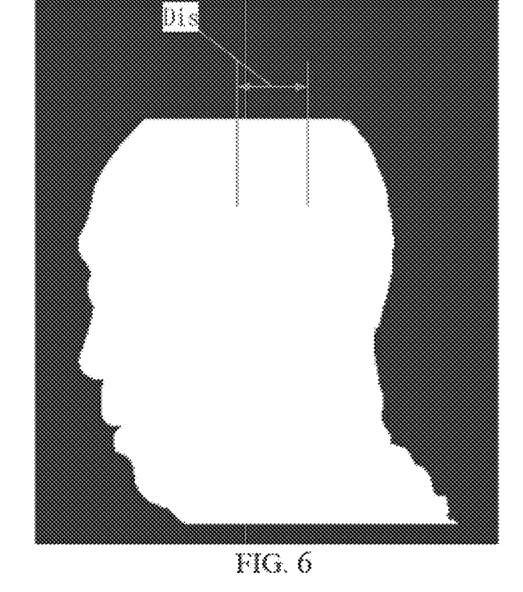
FIG. 6 illustrates a schematic diagram of plain film adjustment according to an embodiment of the present disclosure.

In this embodiment, when the position of the tube focal spot is on the reference plane, in the case where the adjustment direction of the scanning bed is the direction in which the distance between the bed surface of the scanning bed and the ground is increased, i.e., the height of the scanning bed is raised, the adjustment mode of the plain film information may be determined as translating the target scanning object in the plain film information towards the side facing away from the bed surface indicated by the plain film information. On the contrary, in the case where the adjustment direction of the scanning bed is the direction in which the distance between the bed surface of the scanning bed and the ground is reduced, i.e., the height of the scanning bed is lowered, the adjustment mode of the plain film information may be determined as translating the target scanning object in the plain film information towards the side adjacent to the bed surface indicated by the plain film information. For example, as illustrated in FIG. 6, assuming that the target scanning object lies flat on the scanning bed with the face upwards, the side adjacent to the bed surface indicated by the plain film information is a side of the back of the head of the target scanning object. In this case, when the adjustment direction of the scanning bed is the direction in which the height of the scanning bed is raised, the target scanning object in the plain film information is translated towards a side of the nose of the target scanning object. Conversely, when the adjustment direction of the scanning bed is the direction in which the height of the scanning bed is lowered, the target scanning object in the plain film information is translated towards the side of the back of the head of the target scanning object.

In some embodiments, a translation size may be determined based on: calculating a difference between the target bed height and a corresponding height of the scanning bed when the plain film information is obtained, and determining a second adjustment size based on a ratio of the difference to the real physical size.

In this embodiment, the translation size may be referred to as the second adjustment size. As illustrated in FIG. 6, the plain film is the lateral film, in which Dis represents the second adjustment size. The second adjustment size may be represented by the number of pixels. For example, the second adjustment size=(initial bed height-target bed height)/real physical size represented by each pixel. Thus, the second adjustment size is actually the number of pixels by which the region of interest of the plain film moves. The initial bed height is the corresponding bed height of the scanning bed when the plain film information is obtained. The adjusted plain film information, i.e., the target plain film information, may be obtained through translating the region of interest in the plain film based on the second adjustment size.

In the embodiments of the present disclosure, optionally, the method further includes: automatically adjusting the scanning bed to move to the target bed height based on the target bed height.

In this embodiment, after the target bed height is determined, the bed height of the scanning bed may be automatically adjusted to the target bed height. In some embodiments, the bed height of the scanning bed may be adjusted after the target bed height is determined, or may be adjusted after the plain film information is adjusted, as long as the bed height of the scanning bed is adjusted before a rescanning that is based on the target plain film information.

In an example embodiment, the operation at block 102 includes: updating a bed height and/or a bed calibration in the plain film information based on the target bed height to obtain the target plain film information.

Figure 7:
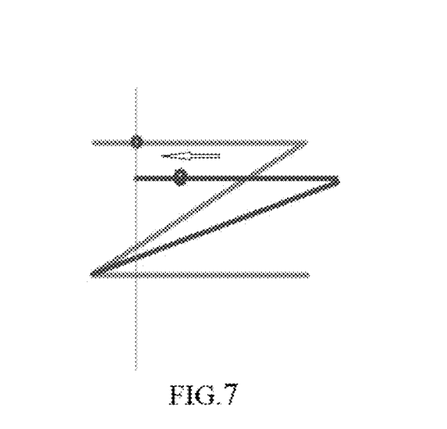
FIG. 7 illustrates a schematic diagram of bed height adjustment of a scanning bed according to an embodiment of the present disclosure.

After the target bed height is determined, information such as the bed height and/or the bed calibration in the plain film information may be correspondingly adjusted and updated to obtain the target plain film information. In the embodiments of the present disclosure, optionally, when the bed height of the scanning bed is adjusted from the initial bed height at the obtained plain film information to the target bed height, supposing that the scanning bed is vertically raised or lowered, the updated plain film information may include bed height information when the plain film information is adjusted; and supposing that the scanning bed is raised or lowered in a zigzag manner, the updated plain film information may include the bed height information and bed calibration information when the plain film information is adjusted. The bed calibration of the scanning bed refers to a scale marked along a length of the scanning bed and is an actual bed calibration. The bed calibration may be marked in a manner that the scale increases gradually from the head of the scanning bed to the tail of the scanning bed, or in a manner that the scale increases gradually from the tail of the scanning bed to the head of the scanning bed. For example, supposing the length of the scanning bed to be 2 meters, the bed calibrations of the scanning bed may be marked from 0 mm to 2,000 mm in millimeter intervals from the head of the scanning bed to the tail of the scanning bed. FIG. 7 is a schematic diagram corresponding to a case where the scanning bed is raised or lowered in the zigzag manner. In this manner, when the bed height of the scanning bed is changed, the bed calibration of the scanning bed is also changed correspondingly. Supposing that FIG. 7 illustrates a side surface of the scanning bed (i.e., a left-hand side or a right-hand side of the patient when the target scanning object lies flat on the scanning bed), the initial bed height is greater than the target bed height, a vertical thin line is a scanning plane, and a dot corresponding to the initial bed height is a target scanning region of the target scanning object. When the bed height of the scanning bed is adjusted to the target bed height, the target scanning region of the target scanning object changes not only in a direction perpendicular to the ground but also in a direction parallel to the ground. In this case, when the target scanning region is scanned at a position corresponding to the scanning plane, the scanning bed may be moved leftwards. That is, the bed calibration of the scanning bed is changed. Therefore, the updated plain film information may further include the bed calibration information when the scanning bed is raised or lowered in the zigzag manner.

Figure 8:
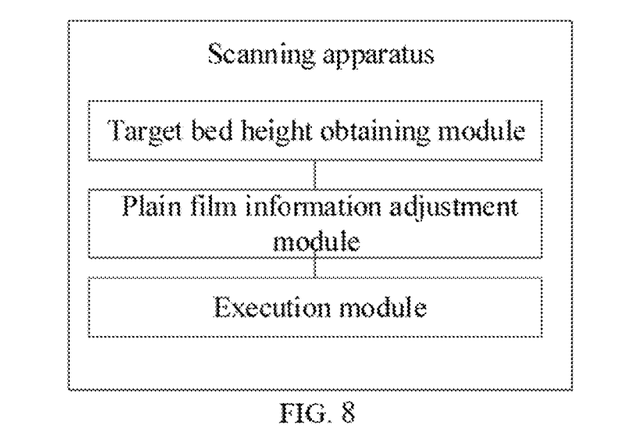
FIG. 8 illustrates a schematic diagram of a structure of a scanning apparatus according to an embodiment of the present disclosure.

Further, as a specific implementation of the method in FIG. 1, embodiments of the present disclosure provide a scanning apparatus. As illustrated in FIG. 8, the apparatus includes a target bed height obtaining module, a plain film information adjustment module, and an execution module. The target bed height obtaining module is configured to obtain plain film information of a target scanning object, and determine a target bed height based on the plain film information. The plain film information adjustment module is configured to adjust the plain film information based on the target bed height to obtain target plain film information. The execution module is configured to perform a subsequent operation based on the target plain film information.

Optionally, the target bed height obtaining module includes a position center determining unit and a target bed height determining unit. The position center determining unit is configured to determine a position center of a region of interest of the target scanning object in a target direction based on the plain film information, the target direction being a direction perpendicular to a bed surface of a scanning bed. The target bed height determining unit is configured to determine the target bed height based on a positional relation between the position center and a scanning center.

Optionally, the position center determining unit is configured to: obtain a target thickness of the region of interest of the target scanning object in the target direction based on the plain film information; and determine the position center of the region of interest of the target scanning object in the target direction based on the target thickness. The plain film information includes a frontal film and/or a lateral filmi.

Optionally, the position center determining unit is further configured to: divide the region of interest indicated by the plain film information into a plurality of sub-regions in a feed direction parallel to the scanning bed, and determine a sub-thickness corresponding to each of the plurality of sub-regions; and obtain a mean value of the plurality of sub-thicknesses, and determine the mean value of the plurality of sub-thicknesses as the target thickness of the region of interest of the target scanning object in the target direction.

Optionally, the plain film adjustment module includes a first determining unit, a second determining unit, and a third determining unit. The first determining unit is configured to determine an adjustment direction of a scanning bed based on the target bed height. The second determining unit is configured to determine an adjustment mode of the plain film information based on the adjustment direction. The third determining unit is configured to adjust the plain film information based on the adjustment mode to obtain the target plain film information.

Optionally, the second determining unit is configured to: obtain a position of a tube focal spot corresponding to the plain film information; determine, based on the adjustment direction when the position of the tube focal spot is on a side of a reference plane, that the adjustment mode of the plain film information is to scale the target scanning object in the plain film information; and determine, based on the adjustment direction when the position of the tube focal spot is on the reference plane, that the adjustment mode of the plain film information is to translate the target scanning object in the plain film information. The reference plane is a plane passing through a scanning center and parallel to a bed surface of the scanning bed.

Optionally, the second determining unit is further configured to: determine, when the adjustment direction is a direction in which a distance between the bed surface of the scanning bed and the tube focal spot is increased, that the adjustment mode of the plain film information is to scale down a size of the target scanning object in the plain film information; and determine, when the adjustment direction is a direction in which the distance between the bed surface of the scanning bed and the tube focal spot is reduced, that the adjustment mode of the plain film information is to scale up the size of the target scanning object in the plain film information.

Optionally, the second determining unit is further configured to: determine, when the adjustment direction is a direction in which a distance between the bed surface of the scanning bed and a ground is increased, that the adjustment mode of the plain film information is to translate the target scanning object in the plain film information towards a side facing away from the bed surface indicated by the plain film information; and determine, when the adjustment direction is a direction in which the distance between the bed surface of the scanning bed and the ground is reduced, that the adjustment mode of the plain film information is to translate the target scanning object in the plain film information towards a side adjacent to the bed surface indicated by the plain film information.

Optionally, a scaling ratio of the operation of scaling the target scanning object in the plain film information and a translation distance of the operation of translating the target scanning object in the plain film information are both positively correlated with a difference between the target bed height and an actual bed height of the scanning bed when obtaining the plain film information.

Optionally, the plain film information adjustment module is further configured to update a bed height and/or a bed calibration in the plain film information based on the target bed height to obtain the target plain film information.

Optionally, the execution module is configured to: select a positioning box based on the target plain film information; obtain scanning parameter information based on the positioning box, the scanning parameter information including a start scanning position and an end scanning position; and adjust an actual bed height of a scanning bed based on the target bed height, and then perform an axial scanning or a spiral scanning based on the scanning parameter information.

It should be noted that reference to other corresponding description of each functional unit involved in the scanning apparatus provided by the embodiments of the present disclosure may be made to corresponding description in the method of FIG. 1 to FIG. 7, and details thereof will be omitted here.

Correspondingly, the embodiments of the present disclosure further provide a storage medium on a basis of the above method as illustrated in FIG. 1 to FIG. 7. The storage medium stores a computer program. The computer program, when executed by a processor, implements the above scanning method as illustrated in FIG. 1 to FIG. 7.

The technical solutions of the present disclosure may be embodied in a form of a software product based on this understanding. The software product may be stored in a non-volatile storage medium (which may be a Compact Disk Read-Only Memory (CD-ROM), a Universal Serial Bus (USB) flash disk, a mobile hard disk, etc.) and includes a number of instructions to cause a computer device (which may be a personal computer, a server, or a network device, etc.) to perform the method described in each implementation scenario of the present disclosure.

To achieve the above objects, the embodiments of the present disclosure further provide a computer device on a basis of the method illustrated in FIG. 1 to FIG. 7 and a virtual apparatus embodiment illustrated in FIG. 8. In particular, the computer device may be a personal computer, a server, a network device, etc. The computer device includes a storage medium and a processor. The storage medium stores a computer program. The processor is configured to execute the computer program to implement the scanning method as illustrated in FIG. 1 to FIG. 7.

Optionally, the computer device may further include a user interface, a network interface, a camera, a radio-frequency (RF) circuit, a sensor, an audio circuit, a wireless fidelity (Wi-Fi) module, etc. The user interface may include a display, an input unit such as a keyboard, etc. Optionally, the user interface may further include a USB interface, a card reader interface, etc. Optionally, the network interface may include a standard wired interface, a standard wireless interface (e.g., a Bluetooth interface, a Wi-Fi interface), etc.

It can be appreciated by those skilled in the art that a structure of the computer device provided by the embodiments of the present disclosure does not constitute a limitation on the computer device. The computer device may include more or fewer components, or combine some components, or have a different arrangement of components.

The storage medium may further include an operating system and a network communication module. The operating system is a program that manages and stores hardware resources and software resources of the computer device, and supports an operation of an information processing program and other software and/or programs. The network communication module is configured to implement communication between components in the storage medium and communicate with other hardware and software in the entity device.

Through the description of the above implementations, those skilled in the art can clearly understand that the present disclosure may be implemented by means of software plus a necessary general hardware platform, or may be implemented by hardware. The target bed height of the scanning bed is determined based on the plain film information, and then the plain film information is adjusted based on the determined target bed height to obtain the target plain film information. Later, the user can perform the subsequent operation based on the target plain film information. According to the embodiments of the present disclosure, the quality of the scanned image is improved while the adjustment efficiency is increased, thereby greatly improving the user experience.

It can be appreciated by those skilled in the art that each accompanying drawing is merely a schematic diagram of a preferred implementation scenario, and modules or processes in the accompanying drawing is not necessarily required for implementing the present disclosure. It can be appreciated by those skilled in the art that modules of the apparatus in the implementation scenario may be distributed in the apparatus in the implementation scenario in accordance with the description of the implementation scenario, or may be located in one or more apparatuses different from the implementation scenario with corresponding changes. The modules in the above-described implementation scenario may be combined into one module, or may be further split into a plurality of sub-modules.

The above sequence numbers of the present disclosure are merely for description, and do not represent superiority or inferiority of the implementation scenario. Only a few specific implementation scenarios of the present disclosure are disclosed above, but the present disclosure is not limited to these specific implementations. Any changes conceivable by those skilled in the art shall fall within the protection scope of the present disclosure.

What is claimed is:

1. A scanning method, comprising:
    obtaining plain film information of a target scanning object, and determining a target bed height based on the plain film information;
    adjusting the plain film information based on the target bed height to obtain target plain film information; and
    performing a subsequent operation based on the target plain film information.

2. The method according to claim 1, wherein said determining the target bed height based on the plain film information comprises:
    determining a position center of a region of interest of the target scanning object in a target direction based on the plain film information, wherein the target direction is a direction perpendicular to a bed surface of a scanning bed; and
    determining the target bed height based on a positional relation between the position center and a scanning center.

3. The method according to claim 2, wherein said determining the position center of the region of interest of the target scanning object in the target direction based on the plain film information comprises:
    obtaining a target thickness of the region of interest of the target scanning object in the target direction based on the plain film information; and
    determining the position center of the region of interest of the target scanning object in the target direction based on the target thickness,
    wherein the plain film information comprises a frontal film and/or a lateral film.

4. The method according to claim 3, wherein said obtaining the target thickness of the region of interest of the target scanning object in the target direction based on the plain film information comprises:
    dividing the region of interest indicated by the plain film information into a plurality of sub-regions in a feed direction parallel to the scanning bed, and determining a sub-thickness corresponding to each of the plurality of sub-regions; and
    obtaining a mean value of the plurality of sub-thicknesses, and determining the mean value of the plurality of sub-thicknesses as the target thickness of the region of interest of the target scanning object in the target direction.

5. The method according to claim 1, wherein said adjusting the plain film information based on the target bed height to obtain the target plain film information comprises:
    determining an adjustment direction of a scanning bed based on the target bed height;
    determining an adjustment mode of the plain film information based on the adjustment direction; and
    adjusting the plain film information based on the adjustment mode to obtain the target plain film information.

6. The method according to claim 5, wherein said determining the adjustment mode of the plain film information based on the adjustment direction comprises:
    obtaining a position of a tube focal spot corresponding to the plain film information;
    determining, based on the adjustment direction when the position of the tube focal spot is on a side of a reference plane, that the adjustment mode of the plain film information is to scale the target scanning object in the plain film information; and
    determining, based on the adjustment direction when the position of the tube focal spot is on the reference plane, that the adjustment mode of the plain film information is to translate the target scanning object in the plain film information,
    wherein the reference plane is a plane passing through a scanning center and parallel to a bed surface of the scanning bed.

7. The method according to claim 6, wherein said determining, based on the adjustment direction when the position of the tube focal spot is on the side of the reference plane, that the adjustment mode of the plain film information is to scale the target scanning object in the plain film information comprises:
- determining, when the adjustment direction is a direction in which a distance between the bed surface of the scanning bed and the tube focal spot is increased, that the adjustment mode of the plain film information is to scale down a size of the target scanning object in the plain film information; and
- determining, when the adjustment direction is a direction in which the distance between the bed surface of the scanning bed and the tube focal spot is reduced, that the adjustment mode of the plain film information is to scale up the size of the target scanning object in the plain film information.

8. The method according to claim 6, wherein said determining, based on the adjustment direction when the position of the tube focal spot is on the reference plane, that the adjustment mode of the plain film information is to translate the target scanning object in the plain film information comprises:
- determining, when the adjustment direction is a direction in which a distance between the bed surface of the scanning bed and a ground is increased, that the adjustment mode of the plain film information is to translate the target scanning object in the plain film information towards a side facing away from the bed surface indicated by the plain film information; and
- determining, when the adjustment direction is a direction in which the distance between the bed surface of the scanning bed and the ground is reduced, that the adjustment mode of the plain film information is to translate the target scanning object in the plain film information towards a side adjacent to the bed surface indicated by the plain film information.

9. The method according to claim 6, wherein a scaling ratio of said scaling the target scanning object in the plain film information and a translation distance of said translating the target scanning object in the plain film information are both positively correlated with a difference between the target bed height and an actual bed height of the scanning bed when obtaining the plain film information.

10. The method according to claim 1, wherein said adjusting the plain film information based on the target bed height to obtain the target plain film information comprises:
- updating a bed height and/or a bed calibration in the plain film information based on the target bed height to obtain the target plain film information.

11. The method according to claim 1, wherein said performing the subsequent operation based on the target plain film information comprises:
- selecting a positioning box based on the target plain film information;
- obtaining scanning parameter information based on the positioning box, the scanning parameter information comprising a start scanning position and an end scanning position; and
- adjusting an actual bed height of a scanning bed based on the target bed height, and then performing an axial scanning or a spiral scanning based on the scanning parameter information.

12. A storage medium, having a computer program stored thereon, wherein the computer program, when executed by a processor, implements:
- obtaining plain film information of a target scanning object, and determining a target bed height based on the plain film information;
- adjusting the plain film information based on the target bed height to obtain target plain film information; and
- performing a subsequent operation based on the target plain film information.

13. The storage medium according to claim 12, wherein said determining the target bed height based on the plain film information comprises:
- determining a position center of a region of interest of the target scanning object in a target direction based on the plain film information, wherein the target direction is a direction perpendicular to a bed surface of a scanning bed; and
- determining the target bed height based on a positional relation between the position center and a scanning center.

14. The storage medium according to claim 13, wherein said determining the position center of the region of interest of the target scanning object in the target direction based on the plain film information comprises:
- obtaining a target thickness of the region of interest of the target scanning object in the target direction based on the plain film information; and
- determining the position center of the region of interest of the target scanning object in the target direction based on the target thickness,
- wherein the plain film information comprises a frontal film and/or a lateral film.

15. The storage medium according to claim 14, wherein said obtaining the target thickness of the region of interest of the target scanning object in the target direction based on the plain film information comprises:
- dividing the region of interest indicated by the plain film information into a plurality of sub-regions in a feed direction parallel to the scanning bed, and determining a sub-thickness corresponding to each of the plurality of sub-regions; and
- obtaining a mean value of the plurality of sub-thicknesses, and determining the mean value of the plurality of sub-thicknesses as the target thickness of the region of interest of the target scanning object in the target direction.

16. The storage medium according to claim 12, wherein said adjusting the plain film information based on the target bed height to obtain the target plain film information comprises:
- determining an adjustment direction of a scanning bed based on the target bed height;
- determining an adjustment mode of the plain film information based on the adjustment direction; and
- adjusting the plain film information based on the adjustment mode to obtain the target plain film information.

17. The storage medium according to claim 16, wherein said determining the adjustment mode of the plain film information based on the adjustment direction comprises:
- obtaining a position of a tube focal spot corresponding to the plain film information;
- determining, based on the adjustment direction when the position of the tube focal spot is on a side of a reference plane, that the adjustment mode of the plain film information is to scale the target scanning object in the plain film information; and
- determining, based on the adjustment direction when the position of the tube focal spot is on the reference plane, that the adjustment mode of the plain film information is to translate the target scanning object in the plain film information, wherein the reference plane is a plane passing through a scanning center and parallel to a bed surface of the scanning bed.

18. The storage medium according to claim 17, wherein said determining, based on the adjustment direction when the position of the tube focal spot is on the side of the reference plane, that the adjustment mode of the plain film information is to scale the target scanning object in the plain film information comprises:
   determining, when the adjustment direction is a direction in which a distance between the bed surface of the scanning bed and the tube focal spot is increased, that the adjustment mode of the plain film information is to scale down a size of the target scanning object in the plain film information; and
   determining, when the adjustment direction is a direction in which the distance between the bed surface of the scanning bed and the tube focal spot is reduced, that the adjustment mode of the plain film information is to scale up the size of the target scanning object in the plain film information.

19. The storage medium according to claim 17, wherein said determining, based on the adjustment direction when the position of the tube focal spot is on the reference plane, that the adjustment mode of the plain film information is to translate the target scanning object in the plain film information comprises:
   determining, when the adjustment direction is a direction in which a distance between the bed surface of the scanning bed and a ground is increased, that the adjustment mode of the plain film information is to translate the target scanning object in the plain film information towards a side facing away from the bed surface indicated by the plain film information; and
   determining, when the adjustment direction is a direction in which the distance between the bed surface of the scanning bed and the ground is reduced, that the adjustment mode of the plain film information is to translate the target scanning object in the plain film information towards a side adjacent to the bed surface indicated by the plain film information.

20. A computer device, comprising:
   a storage medium;
   a processor, and
   a computer program stored in the storage medium and executable by the processor,
   wherein the processor, when executing the computer program, implements:
   obtaining plain film information of a target scanning object, and determining a target bed height based on the plain film information;
   adjusting the plain film information based on the target bed height to obtain target plain film information; and
   performing a subsequent operation based on the target plain film information.

* * * * *